United States Patent [19]

Dobinson et al.

[11] Patent Number: 4,540,769
[45] Date of Patent: Sep. 10, 1985

[54] PREPARATION OF N-GLYCIDYL COMPOUNDS

[75] Inventors: Bryan Dobinson; Michael R. Thoseby, both of Cambridge, England

[73] Assignee: Ciba-Geigy Corporation, Ardsley, N.Y.

[21] Appl. No.: 654,342

[22] Filed: Sep. 25, 1984

[30] Foreign Application Priority Data

Sep. 29, 1983 [GB] United Kingdom ............... 8326118
Sep. 29, 1983 [GB] United Kingdom ............... 8326119

[51] Int. Cl.$^3$ .................. C08G 59/10; C08G 59/28; C07D 301/00; C07D 303/36
[52] U.S. Cl. .................................. 528/90; 528/92; 528/99; 528/223; 528/224; 528/225; 528/229; 528/365; 528/373; 528/391; 528/405; 528/407; 549/514; 549/552
[58] Field of Search .................. 528/92, 99, 223, 224, 528/225, 229, 365, 373, 391, 405, 407; 549/514, 552

[56] References Cited

U.S. PATENT DOCUMENTS

| | | | |
|---|---|---|---|
| 2,951,825 | 9/1960 | Reinking et al. | 549/514 X |
| 4,026,858 | 5/1977 | Andrews et al. | 523/456 |
| 4,101,459 | 7/1978 | Andrews | 528/90 |
| 4,115,296 | 9/1978 | Andrews | 528/92 |
| 4,130,511 | 12/1978 | Andrews | 528/92 |

FOREIGN PATENT DOCUMENTS

| | | |
|---|---|---|
| 865314 | 4/1961 | United Kingdom . |
| 1386594 | 3/1975 | United Kingdom . |
| 2111977 | 7/1983 | United Kingdom . |

OTHER PUBLICATIONS

Encyclopedia Chemical Technology, 3rd Ed., vol. 9, p. 277.

Primary Examiner—Earl Nielsen
Attorney, Agent, or Firm—Luther A. R. Hall

[57] ABSTRACT

Aromatic N-glycidylamines are prepared by treatment of an amine having at least one, and preferably two or more aromatic amino hydrogen atoms, with epichlorohydrin in the presence, as catalyst, of a di- or higher-valent metal salt of nitric or perchloric acid, or of a carboxylic or sulphonic acid substituted by fluorine, chlorine or bromine on the carbon atom alpha to the carboxylic or sulphonic acid group, and dehydrochlorinating the product. The presence of the metal salt gives a product having a higher glycidyl content and a lower viscosity than does the same reaction in the absence of such a salt.

Suitable aromatic amines include aniline, phenylene diamines, phenylene diamines substituted on the aromatic ring and bis(4-aminophenyl)methane. The metal salt may be of, for example, magnesium, calcium, zinc, manganese, nickel, iron, lanthanum, vanadium, ytterbium or uranium.

20 Claims, No Drawings

PREPARATION OF N-GLYCIDYL COMPOUNDS

This invention relates to a process for the preparation of N-glycidyl compounds, more particularly to a process for the preparation of aromatic N-glycidylamines, especially those which are epoxide resins having more than one glycidyl group per average molecule, and to N-glycidylamines made by this process.

Epoxide resins are widely used in industry as adhesives, coatings, castings, insulants, and in reinforced composites, and a variety of chemically distinct epoxide resins are commercially available. Such resins are commonly glycidyl ethers or esters derived from epichlorohydrin and a bisphenol or a dicarboxylic acid, but where good performance at high temperature is required, such as in the aerospace industry, the use of materials having glycidyl groups attached to aromatic amino nitrogen atoms is often preferred. Such materials are prepared by reaction of the aromatic amine with about 0.8–10 equivalents, per amino hydrogen atom, of epichlorohydrin, followed by conventional dehydrochlorination using an alkali. This reaction may be carried out without a catalyst or, as described in British Patent Specification No. 2,111,977, in the presence of an acid catalyst.

Despite their useful properties, N-glycidylamines as conventionally prepared are capable of improvement in two ways. Firstly, the epoxide contents of the products obtained seldom approach the theoretical values for complete glycidylation, i.e., the values that would be found if every amino hydrogen atom were to be replaced by a glycidyl group. The actual epoxide group content varies according to the nature of the amine and, in particular, to the presence or absence of other substituents in the molecule. For example, the epoxide equivalent weight for commercial glycidylated bis(4-aminophenyl)methane is 117–133, according to Kirk-Othmers' Encyclopedia of Chemical Technology, 3rd Edition, Volume 9, page 277. This corresponds to an epoxide content that is 79–90% of that which is theoretically possible. The properties of a cured resin vary according to the epoxide content of the uncured resin: the greater the epoxide content the greater will be the degree of crosslinking and, consequently, the strength of the cured resin. It is clear therefore that a higher epoxide content in the resin would be advantageous.

A second disadvantage of N-glycidylamines as conventionally prepared is that they are often very viscous due, it is believed, to a side reaction occurring during their synthesis in which coupling reactions take place, rather than the desired glycidylation. Such coupling also accounts for the low epoxide contents obtained. Viscous resins are much more difficult to use, especially in the production of fibre-reinforced composites or castings, and hence the use of reactive or inert diluents to reduce this viscosity is often necessary.

The incorporation of diluents is generally held to be undesirable. Reactive diluents are those that react with the curing agent and remain in the cured resin. These tend to have an adverse effect on the properties of the cured resin. Inert diluents are removed by evaporation prior to cure, and these often pose flammability or toxicity hazards. Further, if they are not removed completely from the resin, they also have an adverse effect on cured resin properties.

It has now been found that when N-glycidylation of aromatic amines is catalysed by a di- or higher-valent metal salt of an inorganic oxy-acid, more particularly a metal nitrate or a metal perchlorate, or by a di- or higher-valent salt of a halogen-containing carboxylic or sulphonic acid, more particularly a salt of such an acid which is substituted by one or more halogen atoms on the carbon atom alpha to the carboxylic or sulphonic acid group, products can be obtained having a higher epoxide content and a lower viscosity. A further surprising advantage of the process of the invention is that aromatic amines in which the amino group or groups are sterically hindered by other groups on the molecule may be N-glycidylated with comparative ease, thus extending the range of aromatic amines from which epoxide resins may be prepared.

As an illustration of the disadvantages of methods of preparing N-glycidylamines using known catalysts, it has been found that N-glycidylation using trifluoromethanesulphonic acid as catalyst, as described in the above-mentioned British patent specification No. 2,111,977, gives a relativly poor yield of N-glycidylamine having a low epoxide content and high viscosity.

The use of metal salts of inorganic oxy acids as accelerators for the cure of epoxide resins by amines is known. British Pat. No. 1,464,045 discloses curable compositions comprising (a) an epoxide resin, (b) an aromatic or cycloaliphatic polyamine, and (c) magnesium, calcium, zinc, manganese, cobalt, or nickel perchlorate. British Pat. No. 1,521,356 discloses curable compositions comprising (a) an epoxide resin, (b) an aromatic amino compound, and (c) a nitrate of magnesium or a di- or higher-valent metal of Group IIb, IIIB, IVB, VB, VIB, VIIB or VIII of the Periodic Table.

The use of metal salts of halogenated carboxylic and sulphonic acids as accelerators for the cure of epoxide resins by amines is known. British Pat. No. 1,498,542 discloses compositions, suitable for use as a curing agent for epoxide resins, consisting of (a) a polyamine or a polyaminoamide, amongst others, (b) an aliphatic or araliphatic monocarboxylic acid of 2 to 8 carbon atoms bearing on the carbon atom adjacent to the carboxyl group at least two halogen atoms chosen from fluorine and chlorine atoms, or a salt thereof. Preferred metals, the salts of which are used in compositions containing aromatic amines, are lithium, sodium, calcium and magnesium.

British Pat. No. 1,500,206 discloses compositions, suitable for use as a curing agent for epoxide resins, comprising (a) an aromatic, heterocyclic, or cycloaliphatic polyamine, and, (b) a salt of trifluoromethanesulphonic acid. Preferred salts are those of lithium, calcium, zinc, cadmium, cobalt, nickel, manganese and magnesium.

Despite their use as accelerators for the curing of epoxide resins, it was not known hitherto that metal salts of inorganic oxy acids or halogenated carboxylic or sulphonic acids could be used to catalyse the preparation of N-glycidyl group-containing epoxide resins, nor that the resins so made would have superior properties.

One aspect of this invention therefore comprises a process for the preparation of aromatic N-glycidylamines which comprises heating an amine having at least one and preferably at least two aromatic amino hydrogen atoms with at least 0.7 equivalent, and preferably 0.8 to 1.5 equivalents, per amino hydrogen equivalent of the aromatic amine, of epichlorohydrin, in the presence of a di- or higher-valent metal salt of (a) nitric or perchloric acid or (b) a carboxylic or sulphonic acid substituted by fluorine, chlorine or bromine on the carbon atom alpha to the carboxylic or sulphonic acid group, and dehydrochlorinating the product. Another aspect of this invention comprises aromatic N-glycidylamines prepared by this process.

Preferably, the nitrates and perchlorates used as catalysts in the novel process are those of metals of groups IIA, IIB, IIIB, VIIB or VIII of the Periodic Table, as shown in the Handbook of Chemistry, Lange, 12th Edition published by McGraw-Hill. Nitrates and perchlorates of magnesium, calcium, zinc, manganese, nickel, lanthanum, vanadium (as vanadyl), ytterbium, and uranium (as uranyl) are particularly preferred.

In the salts of halogen-substituted carboxylic and sulphonic acids used as catalysts, the anions are preferably derived from acids having at most 4 carbon atoms. Salts of trifluoroacetic acid, trifluoromethanesulphonic acid, trichloroacetic acid, 2,2-dichloropropionic acid and tribromoacetic acid are especially preferred. The cations of the fluorine-, chlorine- or bromine-substituted carboxylic or sulphonic acids are preferably those of metals of group IIA and transition metals of the Periodic Table of the Elements as shown in the Handbook of Chemistry, Lange, 12th Edition, published by McGraw-Hill. Particularly preferred cations are those of iron, zinc, cadmium and lanthanum and most particularly preferred cations are those of magnesium, vanadium (as vanadyl), manganese, cobalt and nickel.

Specific preferred salts used as catalysts in the process of this invention are magnesium perchlorate, calcium perchlorate, zinc perchlorate, nickel perchlorate, magnesium nitrate, manganese nitrate, lanthanum nitrate, ytterbium nitrate, uranyl nitrate, magnesium trifluoroacetate, manganese trifluoroacetate, nickel trifluoroacetate, vanadyl trifluoroacetate, magnesium trifluoromethanesulphonate, cobalt trifluoromethanesulphonate, magnesium trichloroacetate, magnesium 2,2-dichloropropionate, and magnesium tribromoacetate.

The amount of the salt present in the reaction mixture is generally 0.1 to 10 parts per 100 parts by weight of the aromatic amine, 0.4 to 2 parts per 100 parts of amine being particularly preferred.

The aromatic amine that is glycidylated according to this invention may be solely primary, solely secondary, or it may have both primary and secondary amino groups attached directly to an aromatic ring, and it may have one or a plurality of aromatic rings. Other groups that may be present on such aromatic rings include alkyl groups, especially those of 1 to 4 carbon atoms, alkylene groups of 1 to 4 carbon atoms, sulphonyl groups, halogen atoms, hydroxy groups, alkoxy groups of 1 to 4 carbon atoms, and tertiary amino groups. The preferred amines used in the present process have one or two primary amino groups. Anilines, aminophenylindanes and amines of formula I or II:

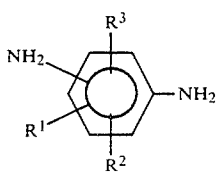

I

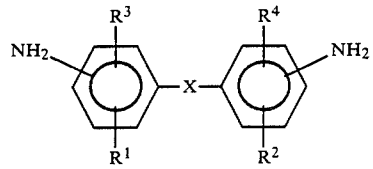

II where
R$^1$, R$^2$, R$^3$, and R$^4$ are the same or different and represent alkyl groups of from 1 to 4 carbon atoms, or hydrogen atoms, and
X represents a valency bond, an alkylene group of from 1 to 4 carbon atoms, an oxygen atom, a sulphur atom or a carbonyl or sulphonyl group,
are particularly preferred.

Examples of particularly preferred amines include aniline, 1,3,3-trimethyl-1-(4-aminophenyl)-5-aminoindane, 1,3,3-trimethyl-1-(4-aminophenyl)-6-aminoindane, o-, m-, and p-phenylenediamine, 2,4-diethyl-6-methyl-1,3-phenylenediamine, bis(4-aminophenyl)methane, bis(4-aminophenyl)ketone, bis(4-aminophenyl)ether, bis(4-aminophenyl)sulphide, bis(3-aminophenyl) and bis(4-aminophenyl)sulphone, 4,4'-diamino-3-ethyldiphenylmethane and bis(4-amino-3-ethylphenyl)methane.

The catalyst is best incorporated into the reaction mixture dissolved in an inert organic solvent such as 2-methoxyethanol, isodecanol, ethylene glycol, diethylene glycol, N-methylpyrrolidone, gamma butyrolactone, benzyl alcohol, dibutyl phthalate, butane-1,4-diol, ethyl methyl ketone, benzene or toluene. The reaction is usually effected in an inert solvent, for example one or more of those listed above, at an elevated temperature, especially at 50° to 100° C. The epichlorohydrin and the catalyst may be added as a single addition, or portionwise, as desired. When the reaction between the amine and epichlorohydrin is judged to be complete, usually within 1 to 5 hours, the dehydrochlorination is effected by conventional means, usually by addition of sodium or potassium hydroxide, optionally together with a quaternary ammonium halide such as benzyltrimethylammonium chloride, as catalyst. After heating at 50°-100° C. for 2-10 hours the mixture is washed with water and the organic phase separated to give the desired N-glycidylamine. This may be used as prepared, or purified, according to conventional practice.

N-glycidyl group-contaning epoxide resins prepared by the process of this invention may be cured in a conventional manner. Thus the invention includes products, such as castings or fibre-reinforced composites, comprising a material obtained by curing an epoxide resin prepared by the process of the invention. Suitable curing agents for N-glycidyl group-containing epoxide resins are well known: they include dicyandiamide, aromatic amines such as bis(3-aminophenyl) and bis(4-aminophenyl)sulphone, and bis(4-aminophenyl)methane (usually together with an accelerator such as a BF$_3$-amine complex), and polycarboxylic acid anhydrides such as cyclohexane 1,2-dicarboxylic acid anhydride, methylbicyclo[2,2,1]-hept-5-ene-2,3-dicarboxylic acid anhydride, pyromellitic acid dianhydride, and benzophenone tetracarboxylic acid dianhydride.

The following Examples illustrate the invention. All parts and percentages are by weight.

EXAMPLE 1

Bis(4-aminophenyl)methane (100 g), toluene (100 ml), and 50% magnesium perchlorate in 2-methoxyethanol (1 g) are stirred and heated to 60° C. Epichlorohydrin (203.5 g) is added portionwise over 2 hours, keeping the temperature between 60° and 90° C. On completion of the addition the mixture is maintained at 80° C. for a further hour.

The mixture is allowed to cool to 75° C. and treated with 50% aqueous benzyltrimethylammonium chloride (6 g). Flake sodium hydroxide (89 g) is added portionwise over 2 hours, after which the mixture is heated at 75° C. for 3 hours. It is then treated with water (300 ml) and toluene (250 ml) with vigorous stirring and filtered. The aqueous layer is discarded and the organic layer washed with a solution (250 ml) containing 1310 parts of water, 450 parts of sodium chloride, and 9 parts of acetic acid. The organic solution is then evaporated in vacuo on a rotary evaporator, redissolved in toluene (250 ml), filtered, and evaporated in vacuo to give a product having an epoxide content of 8.62 equivalents/kg (91% of that theoretically possible) and a viscosity at 40° C. of 46.5 Pa s.

When the experiment is repeated, omitting the magnesium salt catalyst, the epoxide content of the product is 8.37 equivalents/kg (88.3% of theory) and the viscosity at 40° C. is 70.7 Pas.

EXAMPLES 2–7

Example 1 is repeated, replacing the magnesium perchlorate by other salts in 2-methoxy ethanol. The epoxide contents and viscosities of the products are as follows:

| | Catalyst used | | Product | |
|---|---|---|---|---|
| Example | Salt | Quantity (g) | Epoxide content equiv/kg | Viscosity at 40° C. (Pa s) |
| 2 | zinc perchlorate | 2 g | 8.63 | 45.6 |
| 3 | calcium perchlorate | 2 g | 8.54 | 19.6 |
| 4 | lanthanum nitrate | 1 g | 9.03 | 16.1 |
| 5 | ytterbium nitrate pentahydrate | 2 g | 8.96 | 26.2 |
| 6 | uranyl nitrate hexahydrate | 3 g | 8.61 | 44.8 |
| 7 | nickel perchlorate | 2 g | 8.26 | 47.2 |

In Examples 2, 3 and 5–7 salt is added in two equal portions, the first at the commencement of the reaction, and the second on completion of epichlorohydrin addition.

EXAMPLE 8

2,4-Diethyl-6-methyl-1,3-phenylene diamine (100 g) is heated to 65° C. and 50% magnesium perchlorate in methoxyethanol (1 g) added. Epichlorohydrin (207.9 g) is added portionwise over 2 hours, keeping the reaction mixture below 80° C. On complete addition of epichlorohydrin a further quantity of 50% magnesium perchlorate (1 g) is added and the mixture heated at 80° C. for 8 hours. Isopropanol (106 ml) is added and the mixture adjusted to 65° C. 50% aqueous sodium hydroxide (187.2 g) is added portionwise over 2 hours, after which the mixture is heated at 65° C. for a further 2 hours. Water (150 ml) and ethyl methyl ketone (250 ml) are added and the aqueous layer discarded. The organic layer is washed with the brine solution as described in Example 1 (250 ml), evaporated in vacuo on a rotary evaporator, and redissolved in ethyl methyl ketone (250 ml). Filtration and evaporation gives a product having an epoxide content of 7.84 equivalents/kg (78.8% of theory) and a viscosity at 25° C. of 21.5 Pa s.

When the Example is repeated, but omitting the magnesium perchlorate and with an initial reaction time of 16 hours, rather than 8 hours, the product has an epoxide content of 5.67 equivalents/kg (57% of theory) and a viscosity at 25° C. of 581.9 Pa s.

EXAMPLE 9

Example 8 is repeated, using two additions, of 1.5 g each, of 33% magnesium nitrate in methoxy ethanol, in place of magnesium perchlorate. The product has an epoxide content of 7.77 equivalents/kg (78.1% of theory) and a viscosity at 25° C. of 27.5 Pa s.

EXAMPLE 10

Example 1 is repeated, replacing the amine used in that Example by a liquid mixture of bis(4-aminophenyl)methane, 4,4'-diamino-3-ethyldiphenylmethane and bis(4-amino-3-ethylphenyl)methane, and replacing the magnesium perchlorate by lanthanum nitrate. The mixture is heated at 80° C. for 3 hours on completion of the epichlorohydrin addition. The product has an epoxide content of 8.23 equivalents/kg (96.2% of theory) and a viscosity at 25° C. of 17.3 Pa s.

When the experiment is repeated by omitting the lanthanum nitrate catalyst, and using an initial reaction time at 80° C. of 12 hours, rather than 3 hours, the epoxide content of the product is 7.64 equivalents/kg (89% of theory) and the viscosity at 25° C. is 50.3 Pa s.

EXAMPLE 11

Bis(4-aminophenyl)methane (100 g), toluene (150 g) and 50% manganese nitrate in 2-methoxyethanol (1 g) are heated to 60° C. and a vacuum (18665 Pa = 140 mm Hg) is applied. Epichlorohydrin (203.5 g) is added in portions over 1 hour. At the end of the addition the vacuum is broken and the temperature raised to 80° C. Further catalyst solution (1 g) is added and the mixture maintained at 80° C. for 5 hours. 50% aqueous benzyltrimethylammonium chloride (1.5 g) is added and the temperature adjusted to 75° C. Sodium hydroxide (97.1 g) is added in 10 equal portions at 10 minute intervals. At the end of the addition the mixture is maintained at 75° C. for 1 hour, then treated with water (310 mls). The aqueous layer is discarded, and the organic layer is washed with brine solution as described in Example 1, then evaporated in vacuo to give a product having an epoxide content of 8.48 equivalents/kg (89.6% of theory) and a viscosity at 50° C. of 8.6 Pa s.

When the experiment is repeated, omitting the manganese nitrate catalyst, the product has an epoxide content of 7.98 equivalents/kg (84.3% of theory) and a viscosity at 50° C. of 9.8 Pa s.

EXAMPLE 12

Aniline (100 g), toluene (150 g) and 50% lanthanum nitrate in 2-methoxyethanol (1 g) are heated to 60° C. and a vacuum (18665 Pa = 140 mm Hg) is applied. Epichlorohydrin (216.6 g) is added portionwise over 1 hour, after which the vacuum is broken and the temperature raised to 80° C. Further catalyst solution (1 g) is added and the mixture maintained at 80° C. for 4 hours, followed by the addition of 50% aqueous benzyltrimethylammonium chloride (1.5 g) and adjustment of the temperature to 75° C. Sodium hydroxide (103.2 g) is added in 10 equal portions at 10 minute intervals, following which the mixture is maintained at 75° C. for 1 hour and then treated with water (350 ml). The aqueous layer is discarded, and the organic layer is washed with brine solution as described in Example 1 (250 ml), then evaporated in vacuo to give a product having an epoxide content of 9.19 equivalents/kg (94.4% of theory) and a viscosity at 25° C. of 0.09 Pa s.

Repetition of the experiment, omitting the lanthanum nitrate catalyst solution, gives a product having an epoxide content of 3.17 equivalents/kg (32.5% of theory) and a viscosity at 25° C. of 51.1 Pa s.

EXAMPLE 13

Bis(3-aminophenyl)sulphone (50 g), toluene (50 g) and 50% lanthanum nitrate in 2-methoxyethanol (5 g) are heated to 60° C. and a vacuum (18665 Pa=140 mm Hg) is applied. Epichlorohydrin (81.3 g) is added in portions over 1 hour, then the vacuum is broken and the temperature is raised to 80° C. Further catalyst solution (5 g) is added and the mixture is maintained at 80° C. for 6 hours. The temperature is adjusted to 75° C. and the mixture is treated with 50% aqueous benzyltrimethylammonium chloride (0.75 g). Sodium hydroxide (38.7 g) is added in 10 equal portions at 10 minute intervals, after which the mixture is heated at 75° C. for 1 hour, then treated with water (150 ml). The aqueous layer is discarded; the organic layer is washed with brine solution as described in Example 1 (125 ml) and evaporated in vacuo to give a product having an epoxide content of 7.40 equivalents/kg (87.4% of theory) and a viscosity at 50° C. of 456.1 Pa s.

When the experiment is repeated omitting the catalyst solution, very little reaction has occured after carrying out the heating at 80° C. for 6 hours.

EXAMPLE 14

A mixture of 1,3,3-trimethyl-1-(4-aminophenyl) 5- and 6-aminoindances (100 g), toluene (150 g) and 50% lanthanum nitrate in 2-methoxyethanol (1 g) were heated to 60° C. and a vacuum (18665 Pa=140 mm Hg) applied. Epichlorohydrin (151.5 g) is added in portions over 1 hour, then the vacuum is broken and the temperature is raised to 80° C. Further catalyst solution (1 g) is added and the mixture is maintained at 80° C. for 5 hours. The temperature is adjusted to 75° C. and the mixture is treated with 50% aqueous benzyltrimethylammonium chloride (1.5 g). Sodium hydroxide (72.3 g) is added in 10 equal portions at 10 minute intervals, after which the reaction is maintained at 75° C. for 1 hour, then treated with water (250 ml). The aqueous layer is discarded; the organic layer is washed with a brine solution as described in Example 1 (250 ml) and evaporated in vacuo to give a product having an epoxide content of 7.87 equivalents/kg (96.6% of theory) and a viscosity at 50° C. of 121.7 Pa s.

Repetition of the experiment omitting the lanthanum nitrate catalyst solution gives a product having an epoxide content of 6.06 equivalents/kg (74.4% of theory) and a viscosity at 50° C. of 220 Pa s.

EXAMPLE 15

Bis(4-aminophenyl)methane (100 g), toluene (100 ml) and 50% magnesium trifluoromethanesulphonate in 2-methoxyethanol (1 g) are mixed and heated to 60° C. Epichlorohydrin (203.5 g) is added portionwise over two hours, keeping the temperature between 60° and 80° C. and, on complete addition, the mixture is heated at 80° C. for a further hour. It is then cooled to 75° C. and 50% aqueous benzyltrimethylammonium chloride (6 g) is added. The mixture is treated with sodium hydroxide (89 g) which is added portionwise over 2 hours. At the end of the addition the mixture is heated at 75° C. for 3 hours, and water (300 ml) and toluene (250 ml) added with vigorous stirring. The mixture is then filtered and the aqueous layer discarded.

The organic layer is washed with a solution (250 ml) containing 1310 parts of water, 450 parts of sodium chloride, and 9 parts of acetic acid, then evaporated in vacuo on a rotary evaporator. The residue is redissolved in toluene (250 ml) filtered, then evaporated in vacuo to give a product having an epoxide content of 8.87 equivalents/kg (93.6% of the value theoretically possible), and a viscosity at 40° C. of 16.2 Pa s.

When the reaction is repeated, but omitting the magnesium salt catalyst, the product has an epoxide content of 8.37 equivalents/kg (88.3% of theory) and a viscosity at 40° C. of 70.7 Pa s.

EXAMPLES 16–19

Example 15 is repeated, replacing 1 g of magnesium trifluoromethanesulphonate by 2 g of other salts as 50% solutions in methoxyethanol. This salt addition is made in two stages, half being added before addition of epichlorohydrin and the rest on completion of epichlorohydrin addition. Details of the salts, and properties of the products, are as follows:

| Example | Salt used | Epoxide content (equivs./kg) | Viscosity (Pa s) at 40° C. |
|---|---|---|---|
| 16 | magnesium trifluoroacetate | 8.86 | 19.6 |
| 17 | manganese trifluoroacetate | 8.73 | 48.7 |
| 18 | cobalt trifluoromethanesulphonate | 9.12 | 18.5 |
| 19 | nickel trifluoroacetate | 8.40 | 54.3 |

EXAMPLE 20

2,4-Diethyl-6-methyl-1,3-phenylene diamine (100 g) is heated to 65° C. and 50% magnesium trifluoromethanesulphonate in methoxyethanol (1 g) added. Epichlorohydrin (207.9 g) is added portionwise over 2 hours, keeping the reaction mixture below 80° C. On complete addition of epichlorohydrin a further quantity of 50% magnesium trifluoromethesulphonate sulphonate (1 g) is added and the mixture heated at 80° C. for 4 hours. Isopropanol (106 ml) is added and the mixture adjusted to 65° C. 50% aqueous sodium hydroxide (187.2 g) is added portionwise over 2 hours, after which the mixture is heated at 65° C. for a further 2 hours. Water (150 ml) and ethyl methyl ketone (250 ml) are added and the aqueous layer discarded. The organic layer is washed with the brine solution as described in Example 1 (250 ml), evaporated in vacuo on a rotary evaporator, and redissolved in ethyl methyl ketone (250 ml). Filtration and evaporation gives a product having an epoxide content of 7.90 equivalents/kg (79.4% of theory) and a viscosity at 25° C. of 20.0 Pa s.

When the Example is repeated, but omitting the magnesium salt and with an initial reaction time of 16 hours, rather than 4 hours, the product has an epoxide content of 5.67 equivalents/kg (57% of theory) and a viscosity at 25° C. of 581.9 Pa s.

EXAMPLE 21

Example 20 is repeated, using magnesium trifluoroacetate in place of the trifluoromethanesulphonate. The product has an epoxide content of 8.08 equivalents/kg (81.2% of theory) and a viscosity of 25° C. of 31.5 Pa s.

EXAMPLE 33

A liquid mixture of bis(4-aminophenyl)methane, 4,4'-diamino-3-ethyldiphenylmethane and bis(4-amino-3-ethylphenyl)methane (100 g), toluene (100 ml), and 50% magnesium trifluoromethanesulphonate in methoxyethanol (1 g) are stirred and heated together to 60° C. Epichlorohydrin (165.2 g) is added portionwise over 2 hours, keeping the reaction mixture below 80° C. On completion of the addition the mixture is heated at 80° C. for a further 4 hours.

It is cooled to 75° C. and 50% aqueous benzyltrimethylammonium chloride (6 g) added, followed by portionwise addition of sodium hydroxide (72.3 g) over 2 hours. The mixture is heated at 75° C. for 3 hours and then treated with water (250 ml) and toluene (250 ml). The organic layer is separated, washed with brine (250 ml) as described in Example 1, and evaporated. The residue is dissolved in toluene (250 ml), filtered, and evaporated to give a product having an epoxide content of 8.07 equivalents/kg (94.4% of theory) and a viscosity at 25° C. of 33.4 Pa s.

When the Example is repeated, but omitting the magnesium salt and using an initial reaction time at 80° C. of 12 hours rather than 4 hours, the product has an epoxide content of 7.64 equivalents/kg (89% of theory) and a viscosity at 25° C. of 50.3 Pa s.

EXAMPLE 23

Bis(4-aminophenyl)sulphone (100 g), toluene (100 ml), and 50% solution of magnesium trifluoromethanesulphonate in methoxyethanol (1 g) are stirred together and heated to 65° C. Epichlorohydrin (162.5 g) is added portionwise over 2 hours, keeping the temperature of the mixture below 80° C. A further quantity of the magnesium salt solution (1 g) is added and the mixture heated for 13 hours at 80° C., by which time the epoxide content of the mixture is 0.64 equivalents/kg.

The toluene is evaporated in a rotary evaporator and the residue suspended in isopropanol (100 ml). 50% aqueous sodium hydroxide (160 g) is added over 1 hour at 65° C., and the mixture then heated at 65° C. for a further hour. Water (300 ml), and ethyl methyl ketone (300 ml) are added, the aqueous phase is discarded, and the organic layer is washed with brine as described in Example 1 (250 ml) and evaporated. The residue is dissolved in ethyl methyl ketone (250 ml) filtered and evaporated to give a solid product having an epoxide content of 6.46 equivalents/kg (76.2% of theory).

When the experiment is repeated, omitting the magnesium salt, an initial heating for 18 hours at 80° causes only a slight drop in epoxide content (from 5.04 to 4.40 equivalents/kg), indicating that the first stage of the reaction is not taking place.

EXAMPLE 24

Example 11 is repeated, replacing the manganese nitrate solution by a 50% solution of magnesium trichloroacetate in isodecanol. The product has an epoxide content of 9.19 equivalents/kg (97.1% of theory) and a viscosity at 50° C. of 4.1 Pa s.

EXAMPLE 25

Example 12 is repeated, using magnesium trifluoromethanesulphonate in place of the lanthanum nitrate. The product has an epoxide content of 9.18 equivalents/kg (94.3% of theory) and a viscosity at 25° C. of 0.06 Pa s.

EXAMPLE 26

Example 14 is repeated, replacing the lanthanum nitrate by magnesium trifluoromethanesulphonate. A product having an epoxide content of 7.45 equivalents/kg (91.4% of theory) and a viscosity at 50° C. of 84.3 Pa s is obtained.

EXAMPLES 27–29

Example 24 is repeated, replacing the magnesium trichloroacetate solution by 50% solutions of other salts in 2-methoxyethanol. The epoxide contents and viscosities of the products are as follows:

| | | Product | |
|---|---|---|---|
| Example | Catalyst | Epoxide content (equivalents/kg) | Viscosity (Pa s at 50° C.) |
| 27 | vanadyl trifluoroacetate | 8.72 | 7.2 |
| 28 | magnesium tribromoacetate | 8.51 | 7.9 |
| 29 | magnesium 2,2-dichloropropionate | 8.56 | 5.8 |

What is claimed is:
1. A process for the preparation of aromatic N-glycidylamines which comprises
   (i) heating an amine having at least one aromatic amino hydrogen atom with at least 0.7 equivalent, per amino hydrogen equivalent of the amine, of epichlorohydrin, in the presence of a di- or higher-valent metal salt of
   (a) nitric or perchloric acid, or
   (b) a carboxylic or sulfonic acid substituted by fluorine, chlorine or bromine on a carbon atom alpha to the carboxylic or sulfonic acid group, and
   (ii) dehydrochlorinating the product from (i).
2. A process according to claim 1, in which the amine has at least two aromatic amino hydrogen atoms.
3. A process according to claim 1, in which 0.8 to 1.5 equivalents of epichlorohydrin, per amino hydrogen equivalent of the amine, are used.
4. A process according to claim 1, in which the salt used as catalyst is a nitrate or perchlorate of a metal of group IIA, IIB, IIIB, VIIB or VIII of the Periodic Table, or a fluorine-, chlorine- or bromine-substituted carboxylate or sulfonate of a metal of group IIA or a transition metal.
5. A process according to claim 4, in which the salt used is a nitrate or perchlorate of magnesium, calcium, zinc, manganese, nickel, lanthanum, vanadium (as vanadyl), ytterbium, or uranium (as uranyl) or a fluorine-, chlorine- or bromine-substituted carboxylate or sulphonate of iron, zinc, cadmium, lanthanum, magnesium, vanadium (as vanadyl), manganese cobalt or nickel.
6. A process according to claim 5, in which the salt is magnesium perchlorate, calcium perchlorate, zinc perchlorate, nickel perchlorate, magnesium nitrate, manga- nese nitrate, lanthanum nitrate, ytterbium nitrate, or uranyl nitrate.

7. A process according to claim 5, in which the salt has an anion derived from a substituted carboxylic or sulphonic acid having at most 4 carbon atoms.

8. A process according to claim 7, in which the anion is derived from trifluoroacetic acid, trifluoromethane-sulphonic acid, trichloroacetic acid, 2,2-dichloropropionic acid or tribromoacetic acid.

9. A process according to claim 8, in which the salt is magnesium trifluoroacetate, manganese trifluoroacetate, nickel trifluoroacetate, vanadyl trifluoroacetate, magnesium trifluoromethanesulphonate, cobalt trifluoromethanesulphonate, magnesium trichloroacetate, magnesium 2,2-dichloropropionate, or magnesium tribromoacetate.

10. A process according to claim 1, 4 or 5, in which the amount of the salt present is from 0.1 to 10 parts per 100 parts of the amine.

11. A process according to claim 1, in which the catalyst is incorporated into the reaction mixture dissolved in an inert organic solvent.

12. A process according to claim 11, in which the solvent is 2-methoxyethanol, isodecanol, ethylene glycol, diethylene glycol, N-methylpyrrolidone, gamma butyrolacetone, benzyl alcohol, dibutyl phthalate, butane-1,4-diol, ethyl methyl ketone, benzene or toluene.

13. A process according to claim 1, in which the amine has one or two primary amine groups.

14. A process according to claim 13, in which the amine is an aniline, an aminophenylindane or an amine of formula I or II:

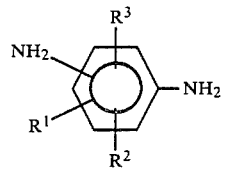

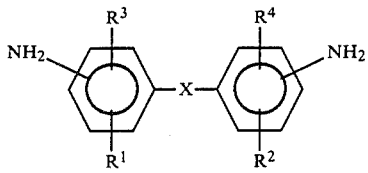

where
$R^1$, $R^2$, $R^3$, and $R^4$ are the same or different and represent alkyl groups of from 1 to 4 carbon atoms, or hydrogen atoms, and
X represents a valency bond, an alkylene group of from 1 to 4 carbon atoms, an oxygen atom, a sulfur atom or a carbonyl or sulfonyl group.

15. A process according to claim 14, in which the amine is aniline, 1,3,3-trimethyl-1-(4-aminophenyl)-5-aminoindane, 1,3,3-trimethyl-1-(4-aminophenyl)-6-aminoindane, o-, m-, or p-phenylenediamine, 2,4-diethyl-6-methyl-1,3-phenylenediamine, bis(4-aminophenyl)methane, bis(4-aminophenyl)ketone, bis(4-aminophenyl)ether, bis(4-aminophenyl)sulfide, bis(3-aminophenyl) or bis(4-aminophenyl)sulfone, 4,4'-diamino-3-ethyldiphenylmethane or bis(4-amino-3-ethylphenyl)methane.

16. A process according to claim 1 which is effected in an inert solvent.

17. A process according to claim 1 which is effected at 50° to 100° C.

18. A process according to claim 1, in which dehydrochlorination is effected by addition of sodium or potassium hydroxide, optionally together with a quaternary ammonium halide as catalyst.

19. An aromatic N-glycidylamine prepared by a process according to claim 1.

20. A material obtained by curing an N-glycidyl group-containing epoxide resin prepared by a process according to claim 1.

* * * * *